US006795795B2

(12) United States Patent
Kreichauf

(10) Patent No.: US 6,795,795 B2
(45) Date of Patent: Sep. 21, 2004

(54) PROBABILISTIC MAP FOR A BUILDING

(75) Inventor: Ruth D. Kreichauf, River Falls, WI (US)

(73) Assignee: Honeywell International Inc., Morristown, NJ (US)

( * ) Notice: Subject to any disclaimer, the term of this patent is extended or adjusted under 35 U.S.C. 154(b) by 33 days.

(21) Appl. No.: 10/171,143

(22) Filed: Jun. 13, 2002

(65) Prior Publication Data

US 2003/0233214 A1 Dec. 18, 2003

(51) Int. Cl.[7] .............................................. G08F 15/00
(52) U.S. Cl. ........................... 702/181; 702/31; 702/94; 702/116; 702/181; 700/50; 700/51; 700/21; 706/52; 706/14; 340/600; 340/627; 714/1
(58) Field of Search .............................. 702/31, 32, 94, 702/95, 104, 116, 122, 181, 123, 179, 180, 190, 195.199, FOR 115, 117, 137, 139, 155, 164, 166, 167, 171; 714/1; 700/50, 51; 706/52, 14; 340/600, 627, 632; 165/2, 11.1, 12, 26

(56) References Cited

U.S. PATENT DOCUMENTS

| | | | |
|---|---|---|---|
| 5,103,405 A | * | 4/1992 | Murphy et al. ................ 395/10 |
| 5,165,465 A | | 11/1992 | Kenet |
| 5,765,636 A | | 6/1998 | Meyer et al. |
| 5,952,569 A | | 9/1999 | Jervis et al. |
| 2001/0047628 A1 | * | 12/2001 | Mouton et al. ................ 52/144 |
| 2002/0098794 A1 | * | 7/2002 | Krafthefer ................... 454/370 |
| 2003/0020618 A1 | * | 1/2003 | Hemmer et al. ............. 340/632 |
| 2003/0065409 A1 | * | 4/2003 | Raeth et al. .................... 700/31 |

OTHER PUBLICATIONS

CBNP–Strategic Plan–Program Structure–Modeling & Prediction, "Chemical & Biological National Security Program," http://www.nn.doe.gov/cbnp/modeling.shtml, 2 pages, downloaded Jul. 11, 2001.

Alamdari, F., Edwards, S.C., Hammond, S.P., Microclimate performance of an open atrium office building: *a case study in thermo–fluid modeling*, pp. 81–92.
Alani, A., Barton, I.E., Seymour, M.J., Wrobel, L.C., "Contaminants Transport Modeling," pp. 1–9.
Pollock, G., Stribling, D., "A Real Application of Airflow Modelling in Optimising Cleanroom Design," Jul. 12, 2001.
Databases and Software —Non–EPA, http://www.epa.gov/ceppo/ds–noep.htm, pp. 1–21, downloaded Jul. 12, 2001.
MIDAS–AT Meteorological Information and Dispersion Assessment System Anti–Terrorism, http://www.midas–at.com/midas–at.html, pp. 1–10, downloaded Jul. 11, 2001.
Decisive Advantages Of MIDAS–AT, http://www.midas–at.com/ppt/midas–81898b/WEB%20Site–81898/sld004.htm, 1 page, downloaded Jul. 11, 2001.
MIDAS–AT Has Extensive Data Retrieval Capabilities, http://www.midas–at.com/lppt/midas–81898b/WEB%20Site–81898/sld012.htm, 1 page, downloaded Jul. 11, 2001.
Inside Building Model, http://www.midas–at.com/ppt/midas–81898b/WEB%20Site–81898/sld016.htm, 1 page, downloaded Jul. 11, 2001.

(List continued on next page.)

*Primary Examiner*—Marc S. Hoff
*Assistant Examiner*—Elias Desta
(74) *Attorney, Agent, or Firm*—Kris T. Fredrick

(57) ABSTRACT

A probabilistic map generator for indicating the probability of a chemical, biological or other agent in a structure or building. The building is mapped in to floors and several levels of cubes in each floor. The probability of an agent's presence is indicated for each cube. Sensors are placed in various locations on each floor of the building. Inputs from the sensors go to a data processor. The probabilities of an agent's presence may be calculated by the data processor in conjunction with a Kalman filter. The probabilities may be displayed in a diagram of cubes, each having a certain shading indicating a probability of the agent's presence for the respective cube.

36 Claims, 3 Drawing Sheets

OTHER PUBLICATIONS

Inside Building Model: Room Representation, http://www.midas–at.com/ppt/midas–81898b/WEB%20/Site–81898/sld017.htm, 1 page, downloaded Jul. 11, 2001.

Inside Building Model: Room Representation, http://www.midas–at.com/ppt/midas–81898/WEB%20Site–81898/sld018.htm, 1 page, downloaded Jul. 11, 2001.

Inside Building Model: Results, http://www.midas–at.com/ppt/midas–81898b/WEB%20Site–81898/sld019.htm, 1 page, downloaded Jul. 11, 2001.

PLG Home Page—MIDAS–AT, http://www.midas–at.com/plg–at.com/plg–home.html, pp. 1–2, downloaded Jul. 11, 2001.

MIDAS–Chemical and Petrochemical Industry Applications, http://www.midas–at.com/midas–chem.html, pp. 1–2, downloaded Jul. 11, 2001.

Dispersion Modeling For Release Of Toxic Substances, http://www.plg.com/pages/model.html, pp. 1–3, downloaded Jul. 11, 2001.

MIDAS–AT, http://www.ege.com/midas.html, pp. 1–4, downloaded Jul. 11, 2001.

Marine unit buys attack–modeling software, http://www.fcw.com/few/articles/1999/FCW_101899_50.asp, pp. 1–2, downloaded Jul. 12, 2001.

* cited by examiner

PROBABILISTIC MAP FOR A BUILDING

BACKGROUND

The invention pertains to detection of dangerous agents in the air. More particularly, the invention pertains to detecting the presence and movement of a chemical or biological agent in a building.

SUMMARY

The invention provides a probabilistic map with the likelihood of a location and a concentration of a chemical or biological agent in various portions of a building or structure during and/or after an attack.

DESCRIPTION

Figure 1:
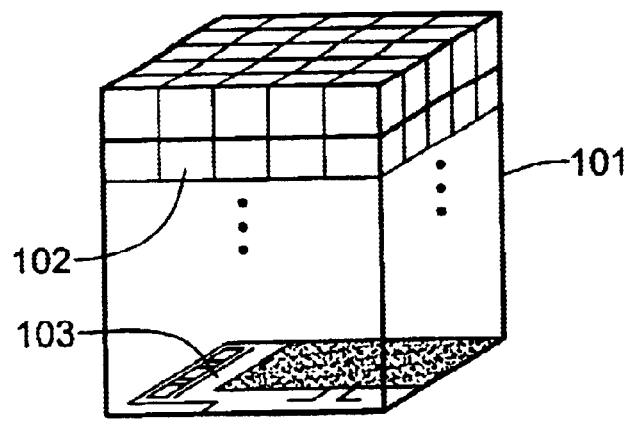
FIG. 1 is a three-dimensional representation of a building floor divided up into subvolumes or cubes.

A probabilistic map shows regions with high to low probability indications of a presence of a chemical or biological agent or other substance or agent in a building or structure. The map is three dimensional in scope and may include information about building levels, ductwork and other building components. The map is updated continuously in time and space so as to provide information for a timely and targeted control response. It contains information noting the randomness of the sensor readings due to air movement, different points of attack, inaccurate sensor readings and the discrete nature of sensor locations in the building. The probabilities indicated by the map may be continuous in space to provide safe evacuation routes for the building inhabitants. The probability map may be stored to provide forensic material by observing the evolution of the map in time and space. The map may provide information for optimal placement of additional sensors in areas where the map does not provide full information. It may be based on first principles of building models. The map may provide information for computational reduction for fluid dynamic calculations by specifying special areas of concern.

During a chemical or biological attack, measurements by sensors used to collect information always introduce randomness, due to reasons of air movement, different points of attack, inaccurate sensor readings and due to the discrete nature of sensor location. In the event of such an attack, it would be useful to create a probability map of the building and estimate the agent concentration and location.

The driving mechanism of the map would be an application of an extended Kalman filter. The outcomes of the filter are the state estimates of location and concentration of the agent in the building. A good structural model of the building environment, as well as measurement data and a measurement model, needs to be available. The filter uses a mix between "continuous" state updates and "discrete" Kalman filter/measurement updates that occur when useful new measurements come in.

There are various forms of dynamic building models currently available that can be used to continuously simulate/update the building states. Those states should include pressures, flow, agent concentration and agent location. Parameters that describe the building model are the geometry of the building, outside conditions, sensor location and number of sensors, agent properties, as well as agent release location and agent amount. Control inputs to the Kalman filter include the changing HVAC system settings, i.e., opening and closing dampers, fan speeds, and so forth. During the period of time where there are not any measurements available, the Kalman filter propagates and predicts its states continuously using the dynamic building model. As soon as there are sensor measurement data available, the Kalman filter updates its state estimates using the new measurement data.

An advantage of using the Kalman filter is its use for online estimation and prediction of the model states. It can be updated continuously in time and space, to provide information for a timely and targeted control response. The Kalman filter describes regions of high to low probability indicating the presence of a chemical or biological agent by displaying information of the error and measurement covariance matrices of the Kalman filter. The map incorporates information indicating the randomness mentioned in the introduction by calculating standard deviations that are a direct outcome of the state estimate updates. The evolution of the Kalman filter states and covariance matrices in time and space should be stored to provide forensic material.

Figure 2A:
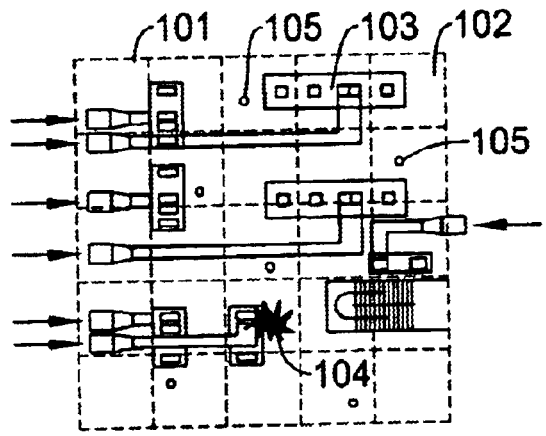
FIG. 2a shows a plan view of the floor of a building with an overlay of cube boundaries.
Figure 2B:
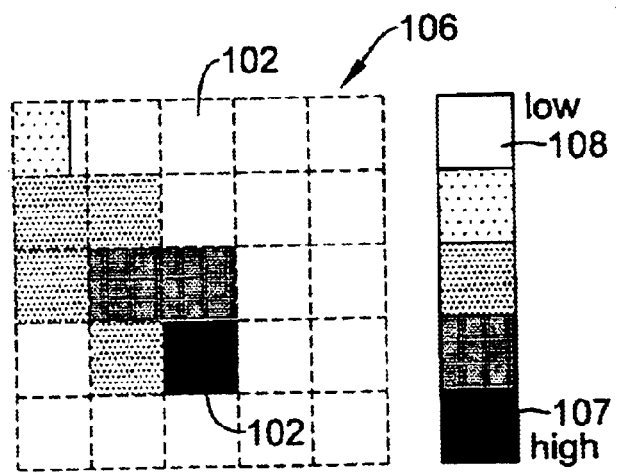
FIG. 2b is a probabilistic map of the floor according to the cubes or subvolumes of the floor.

FIG. 1 is a schematic of an illustrative floor 101 of a building that a probabilistic map of agent distribution will represent. The volume of floor 101 is divided into cubes or subvolumes 102. The cube density may be changed. There may be as many levels of cubes 102 and as many cubes in a layer as desired. A pattern 103 at the bottom of floor 101 may reveal the various features, stairwells, vents, sensors 105 and so forth in floor 101. A plan view or pattern 103 of the floor 101 is also shown in FIG. 2a. A particular floor 101 of a building along with a particular level of cubes is represented in FIG. 2a. Cubes 102 are indicated by the dashed lines. FIG. 2b is an example of a probabilistic map 106 of floor 101 at a selected level of cubes 102. The various shades of the block indicate the level of likelihood of the presence of an agent in a particular cube. The darker shading 107 indicates a greater probability of the presence of an agent than a lighter shading 108.

An agent release, for an illustrative example, is shown by symbol 104 in FIG. 2a. A block 102 in probabilistic map 106 corresponding to block 102 in FIG. 2a corresponding to the same volume, is black and represents a high probability of the presence of an agent. Probabilistic map 106 may be configured to indicate, besides location, the concentration of the agent. Probabilistic map 106 may represent cubes in a side view as desired. Map 106 may be a three-dimensional representation of cubes 102 for one level of cubes 102 in a floor 101 or all levels of cubes 102 of floor 101, or all cubes 102 for the whole building.

Figure 3:
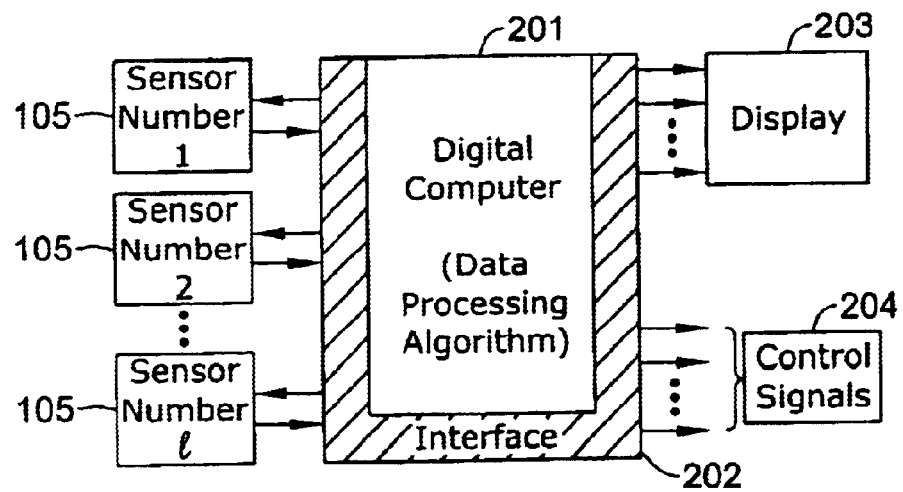
FIG. 3 is a diagram of hardware used for the probabilistic map generator or system.

FIG. 3 shows an illustrative example of the basic hardware used to implement the invention. A digital computer 201 is used for processing input signals from sensors or sensor suite 105 via an interface 202. Computer 201, in FIG. 3, contains not just a processing mechanism, but also a database which includes the building and transport models.

Also, processor 201 of this figure contains Kalman filter 407, a data processing algorithm. A probabilistic map 106 output is provided to display indicator 203 for observation by an operator. Control or recommended action signals 204 may be output of the probabilistic map 106 system.

Figure 4:
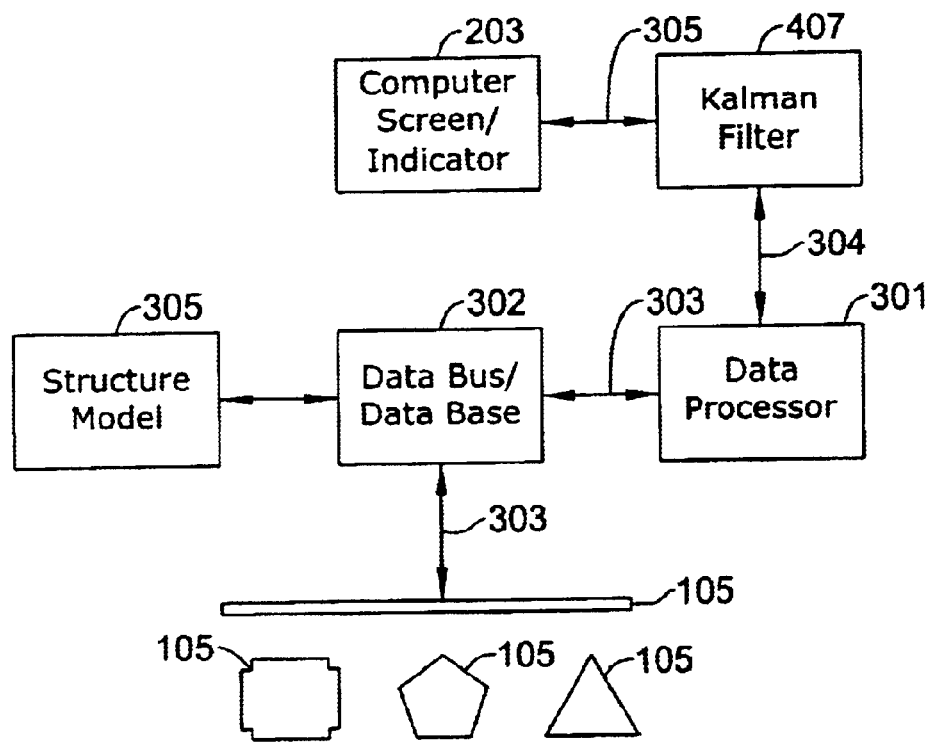
FIG. 4 is a diagram of the hardware and Kalman filter of the map system.

FIG. 4 is like FIG. 3 except Kalman filter 407 and data bus and database 302 are delineated from digital computer or data processor 301. Processor 301 may have a database connected to it. Data 303 from specialty sensors or sensor mechanism 105 may go to data bus 302. Control signals 303 may go to control various aspects of sensors 105. Sensors 105 may sense pressure, flow, temperature, agent composition and concentration, and other things. A structure model 305 having parameters is connected to data bus/database 302. Data bus 302 is like an interface between data processor 301 and sensors 105. Data processor 301 passes building systems information 304 to Kalman filter 407 and filter 407 provides filter-processed information 304 to data processor 301. Kalman filter 407 algorithmically processes out probabilistic information 305 for a probabilistic map 106 to be displayed on computer screen or display 203. Computer screen or display 203 may have a console or keyboard proximate to it for controlling data processor or computer 201.

A continuous-discrete extended Kalman filter is utilized for the probabilistic map. The system model equation is:

$$\dot{\underline{x}}(t) = \underline{f}(\underline{x}(t),t) + \underline{w}(t), \text{ where } \underline{w}t \sim N(\underline{0}, Q(t))$$

The system model $\underline{x}(t)$ is a state space representation of the building model and an agent transport model. Transport of the agent is affected by the building model and the transport model. $\underline{f}(x(t))$ is a portion of the equation that is the essence of the system model which includes the building and transport models. $\underline{f}$ incorporates parameters of the building model such as the dimensions of the building. $\underline{w}(t)$ is process noise. It represents other conditions or external influences like weather. More accurate models should reduce $\underline{w}(t)$. However, with more accurate models the computation time increases. $\underline{w}(t)$ follows $N(0,Q(t))$ where N indicates a normal distribution of the noise model.

The equation for the measurement model is:

$$\underline{z}_k = \underline{h}_k(x(t_k)) + \underline{v}_k, \text{ where } K=1, 2, \ldots \text{ and } \underline{v}_k \sim N(\underline{0}, R_k).$$

The measurement model involves measurements of the agent (what kind is indicated by a chemical sensor), location and concentration of the agent, the pressure and/or flow, and the temperature. $X(t_k)$ indicates measurements made at time t at discrete instances k. $V_k$ indicates the noise on the measurements. The noise is integrated into the Kalman filter calculations. The measurement noise $V_k \sim N(\underline{0}, R_k)$ follows a normal distribution.

The equation for the initial conditions is $\underline{x}(0) \sim N(\hat{\underline{x}}_0, P_0)$. $\underline{x}(0)$ is the initialization of the states. $N(\hat{\underline{x}}_0, P_0)$ indicates the certainty of the initial estimate. The initial values of measurements involve pressure and/or flow, temperature, agent location which indicates no agent to be present, and a zero agent concentration. The other assumptions are stated as $E[\underline{w}(t)\underline{v}_k^T]=0$ for all k and all t, i.e., measurement noise and process noise are independent from each other.

The state estimate propagation or system model continuous update is indicated by $\dot{\hat{\underline{x}}}(t) = \underline{f}(\hat{\underline{x}}(t),t)$. The error covariance propagation is indicated by:

$$\dot{P}(t) = F(\hat{\underline{x}}(t),t)P(t) + P(t)F^T(\hat{x}(t),t) + Q(t).$$

$F(\hat{\underline{x}}(t),t)$ is a linearized representation of the system model. It is a Jacobian matrix as shown by the following equation evaluated at previous state estimates.

$$F(\hat{x}(t), t) = \left. \frac{\partial \underline{f}(\underline{x}(t), t)}{\partial x(t)} \right|_{\underline{x}(t)=\hat{\underline{x}}(t)}$$

The state estimate update for the system model is a discrete update that is indicated by the following equation.

$$\hat{\underline{x}}_k(+) = \hat{\underline{x}}_k(-) + K_k[\underline{z}_k - \underline{h}_k(\hat{\underline{x}}_k(-))].$$

$Z_k\_z$, is truth minus estimate which equals the error. The Kalman filter is discretely updated with this error. Such updates may occur every several seconds or less. The error covariance update is:

$$P_k(+) = [I - K_k H_k(\hat{\underline{x}}_k(-))]P_k(-).$$

$P_k$ is a covariance matrix and $K_k$ is a common gain matrix. $K_k$ is represented by the following equation:

$$K_k = P_k(-)H_k^T(\hat{\underline{x}}_K(-))\left[H_k(\hat{\underline{x}}_k(-))P_k(-)H_k^T(\hat{\underline{x}}_k(-)) + R_k\right]$$

$H_k(\hat{\underline{x}}_k(-))$ is a measurement matrix which is represented by the following equation—a linearized version of the measurement model.

$$H_k(\hat{x}_k(-)) = \left. \frac{\partial \underline{h}_k(\underline{x}(t_k))}{\partial x(t_k)} \right|_{\underline{x}(t_k)=\hat{\underline{x}}_k(-)}$$

Figure 5:
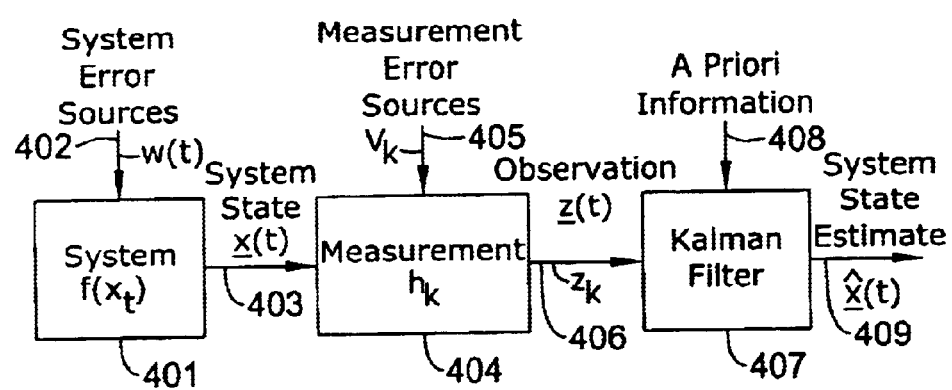
FIG. 5 is a diagram of the system, measurement and Kalman filter aspects of the probabilistic map system.

FIG. 5 is a block diagram depicting the system, measurement and estimator portions of the Kalman filter aspect of the probabilistic map generator for a building. System $f(x_t)$ block 401 has system error sources w(t) input 402 to system 401. An output 403 passes system state $\underline{x}(t)$ information to measurement $h_k$ block 404. This information includes pressure and/or flow within the building, and the location and concentration of an agent within the building. Also, measurement error sources $V_k$ information 405 passes on to block 404. An output $Z_k$ 406 consists of observation $\underline{z}(t)$ information that goes to Kalman filter 407. A priori information goes to Kalman filter 407 via input 408. An output 409 of Kalman filter 407 provides system state estimate $\hat{\underline{x}}(t)$ information.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. An apparatus for generating a probabilistic map of an agent in a building, comprising:

a processor;

a database connected to said processor;

a sensing mechanism in the building connected to said processor; and wherein:

said database has a model of the building;

data from said sensing mechanism may be processed by said processor for input to said model; and the model has a volume divided into subvolumes to identify various places in the building, and wherein each subvolume indicates a probability that an agent may be in a subvolume of the building.

2. The apparatus of claim 1, further comprising a filter connected to said processor.

3. The apparatus of claim 2, further comprising an indicator connected to said processor.

4. The apparatus of claim 3, wherein said indicator is able to display the probability of each subvolume of the model.

5. The apparatus of claim 4, wherein each floor of the building represented in the model has a plurality of subvolumes.

6. The apparatus of claim 5, wherein each floor of the building has a plurality of levels of subvolumes.

7. The apparatus of claim 6, wherein said filter provides state estimates of location and concentration of an agent in the building, which can be indicated by the respective subvolumes of the model.

8. The apparatus of claim 7, wherein said filter uses continuous state updates and discrete updates upon a receipt of new data from said sensing mechanism.

9. The apparatus of claim 8, wherein said filter provides state estimates of pressure and/or flow in the building which can be indicated by the respective subvolumes of the model.

10. The apparatus of claim 9, wherein said filter comprises parameter inputs comprising:

building geometry;

conditions external to the building; and/or sensor descriptions and locations.

11. The apparatus of claim 10, wherein said filter comprises control inputs comprising at least some various heat, ventilation and air conditioning settings.

12. The apparatus of claim 11, wherein said filter is a Kalman filter.

13. A probabilistic map generator comprising:

a processor;

a sensor suite connected to said processor; and a Kalman filter connected to said processor; and wherein said Kalman filter and processor process data from said sensor suite into a probabilistic map.

14. The generator of claim 13, wherein:

said sensor suite is a set of sensors situated in a volume;

the volume comprises subvolumes;

the probabilistic map indicates a probability of an agent's presence in at least one subvolume.

15. The generator of claim 14, wherein:

the volume is a building; and the parameter inputs of the building are entered into said processor.

16. The generator of claim 15, wherein the probabilities of the at least one subvolume may be displayed.

17. A method for generating a probabilistic map, comprising:

taking data from a plurality of sensors situated in a structure;

entering the data into a processor;

constructing a model having parameters of the structure;

entering the model and parameters into the processor; and processing with a Kalman filter the data and parameters into probabilities of an agent in the structure.

18. The method of claim 17, further comprising:

segregating the model into subvolumes; and processing a probability of an agent in each subvolume.

19. The methods of claim 18, further comprising displaying the probabilities in a map of subvolumes of the model of the structure.

20. A probabilistic map generator comprising:

means for sensing data in a structure;

means for processing connected to said means for sensing;

means for modeling the structure, connected to said means for processing;

means for Kalman filter processing connected to said means for processing; and means for displaying a probabilistic map, connected to said means for Kalman filter processing.

21. An apparatus for generating a probabilistic map of an agent in a building, comprising:

a processor;

a database connected to the processor;

a sensing mechanism in the building connected to the processor;

a filter connected to the processor; and an indicator connected to the processor; and wherein:

the database has a model of the building;

data from the sensing mechanism may be processed by the processor for input to the model;

the model has a volume divided into subvolumes to identify various places in the building;

each subvolume indicates a probability that an agent may be in a subvolume of the building;

indicator is able to display the probability of each subvolume of the model;

each floor of the building represented in the model has a plurality of subvolumes;

each floor of the building has a plurality of levels of subvolumes; and the filter provides state estimates of location and concentration of an agent in the building, which can be indicated by the respective subvolumes of the model.

22. The apparatus of claim 21, wherein the filter uses continuous state updates and discrete updates upon a receipt of new data from the sensing mechanism.

23. The apparatus of claim 22, wherein the filter provides state estimates of pressure and/or flow in the building which can be indicated by the respective subvolumes of the model.

24. The apparatus of claim 23, wherein the filter comprises parameter inputs comprising:

building geometry;

conditions external to the building; and/or sensor descriptions and locations.

25. The apparatus of claim 24, wherein the filter comprises control inputs comprising at least some various heat, ventilation and air conditioning settings.

26. An apparatus for generating a probabilistic map of an agent in a building, comprising:

a sensing mechanism in the building;

a filter;

an indicator;

a processor connected to the sensing mechanism, the filter and the indicator; and a database connected to the processor; and wherein:

the database has a model of the building;

data from the sensing mechanism is processed by the processor for input to the model;

the model has a volume divided into subvolumes to identity various places in the building;

each subvolume indicates a probability that an agent may be in a subvolume of the building;

indicator is able to display the probability of each subvolume of the model; and the filter provides state estimates of location and concentration of an agent in the building, according to the respective subvolumes of the model.

27. The apparatus of claim 26, wherein the filter uses continuous state updates and discrete updates upon a receipt of new data from the sensing mechanism.

28. The apparatus of claim 27, wherein the filter provides state estimates of pressure and/or flow in the building which is indicated by the respective subvolumes of the model.

29. The apparatus of claim 26, wherein the filter comprises parameter inputs comprising:

building geometry;

conditions external to the building; and/or sensor descriptions and locations.

30. The apparatus of claim 29, wherein the filter comprises control inputs comprising at least some various heat, ventilation and air conditioning settings.

31. An apparatus for generating a probabilistic map of a chemical/biological agent in a building, comprising:

an agent sensing mechanism in the building;

a filter;

an indicator;

a processor connected to the agent sensing mechanism, the filter and the indicator; and a database connected to the processor, and wherein:

the database comprises a model of the building;

data from the sensing mechanism is processed by the processor for input to the model;

the model has a volume divided into subvolumes to represent various subvolumes in the building, and wherein each subvolume of the model based on data from the processor indicates a probability that an agent is in a corresponding subvolume of the building; and the indicator displays the probability of each subvolume of the model.

32. The apparatus of claim 31, wherein each floor of the building represented in the model has a plurality of subvolumes.

33. The apparatus of claim 32, wherein the filter has parameter inputs comprising:

building geometry;

conditions external to the building; and sensor descriptions and locations.

34. The apparatus of claim 33, wherein:

the filter provides state estimates of location and concentration of an agent in the building, which are indicated by the respective subvolumes of the model; and the filter uses continuous state updates and discrete updates upon a receipt of new data from the sensing mechanism.

35. The apparatus of claim 34, wherein the filter provides state estimates of pressure and flow in the building are indicated by the respective subvolumes of the model.

36. The apparatus of claim 35, wherein the filter comprises control inputs comprising at least some various heat, ventilation and air conditioning settings.

* * * * *